United States Patent [19]
Terry

[11] Patent Number: 5,980,928
[45] Date of Patent: Nov. 9, 1999

[54] IMPLANT FOR PREVENTING CONJUNCTIVITIS IN CATTLE

[76] Inventor: Paul B. Terry, 1605 Independence Dr., Plattsburg, Mo. 64477

[21] Appl. No.: 08/902,113

[22] Filed: Jul. 29, 1997

[51] Int. Cl.[6] ................................................ A61F 2/00
[52] U.S. Cl. .................. 424/427; 424/428; 424/423; 514/914; 514/954; 514/955; 623/4; 623/5; 623/6; 604/289; 604/890.1; 604/891.1
[58] Field of Search ........................... 514/954, 955, 514/914; 424/427, 428, 423; 623/4–6; 604/289, 890.1, 891.1

[56] References Cited

U.S. PATENT DOCUMENTS

| | | | |
|---|---|---|---|
| 4,117,115 | 9/1978 | Hutchins | 424/148 |
| 4,117,842 | 10/1978 | Hutchins | 128/163 |
| 4,135,514 | 1/1979 | Zaffaroni et al. | 128/260 |
| 4,254,098 | 3/1981 | Graham, Jr. et al. | 424/14 |
| 4,259,320 | 3/1981 | De Lay | 424/118 |
| 4,478,935 | 10/1984 | Williams et al. | 435/75 |
| 4,654,334 | 3/1987 | Williams et al. | 514/184 |
| 4,660,546 | 4/1987 | Herrick et al. | 128/1 R |
| 4,846,844 | 7/1989 | De Leon et al. | 623/66 |
| 4,911,641 | 3/1990 | Detsch | 433/228.1 |
| 4,952,419 | 8/1990 | De Leon et al. | 427/2 |
| 5,019,096 | 5/1991 | Fox, Jr. et al. | 623/1 |
| 5,049,142 | 9/1991 | Herrick et al. | 604/294 |
| 5,053,030 | 10/1991 | Herrick et al. | 604/890.1 |
| 5,073,114 | 12/1991 | Detsch | 433/228.1 |
| 5,163,959 | 11/1992 | Herrick | 623/11 |
| 5,171,270 | 12/1992 | Herrick | 623/11 |
| 5,217,493 | 6/1993 | Raad et al. | 623/11 |
| 5,263,923 | 11/1993 | Fujimoto | 602/62 |
| 5,268,178 | 12/1993 | Calhoun et al. | 424/426 |
| 5,414,011 | 5/1995 | Fu et al. | 514/413 |
| 5,545,409 | 8/1996 | Laurencin et al. | 424/426 |
| 5,554,187 | 9/1996 | Rizzo, III | 623/6 |
| 5,567,431 | 10/1996 | Vert et al. | 424/426 |

OTHER PUBLICATIONS

Biosis AN 88:68681, Greer et al., *Scanning Microsc.*, 1 (2), 863–870, 1987.

*Primary Examiner*—Michael P. Woodward
*Assistant Examiner*—C. Delacroix-Muirheid
*Attorney, Agent, or Firm*—Litman, Kraai & Brown L.L.C.; John C. McMahon

[57] ABSTRACT

A method to reduce the likelihood of conjunctivitis in farm animals, especially cattle, includes the step of injecting an implant containing an antibiotic effective against the microbes associated with conjunctivitis subcutaneously into the animal in close proximity to the eye. Preferably the implant includes a matrix to allow time release of the antibiotic and the implant is placed in the animal near the first part of July. Also preferably the antibiotic is tetracycline.

12 Claims, 1 Drawing Sheet

IMPLANT FOR PREVENTING CONJUNCTIVITIS IN CATTLE

BACKGROUND OF THE INVENTION

The present application is directed to a method of controlling a conjunctivitis known as "pinkeye", in cattle and other livestock by placing a subcutaneous antibiotic implant in close proximity to each eye of an animal to be treated in accordance with the method.

Pinkeye is the common name for a conjunctivitis or inflammation of the conjunctiva. This conjunctivitis can result in ulceration of the eyeball, severe pain, blepharospasm, excess tearing and eventually corneal perforation with subsequent prolapse of the intraocular contents, blindness, weight loss and substantial decrease in value to the owner. Because of the colorization of the eyeball, the disease is commonly known as pinkeye. Various microbes may be associated with the inflammation with the most common being one or more of the strains of Moraxella Bovis.

While microbes are associated with the inflammation, there appear to be different opinions as to the exact primary and secondary causes of conjunctivitis in cattle and as to what events must occur to result in such an inflammation. Obviously, there must be some exposure to the infecting microbe.

It may also be necessary to have some exposure to ultraviolet radiation which can be provided by the sun and/or other factors including dust, weed growth, stresses that compromise the animal's defense system, and insect, especially fly, infestation. Flies also may transport and transmit the infectious bacteria between animals. Most cases of conjunctivitis in the northern hemisphere occur during what is referred to as the peak period for conjunctivitis: during the period extending from July to October. This also correlates with the period of greatest sunshine and with the greatest incidence of the other noted factors.

Conjunctivitis can lead to serious problems, as noted above and is especially troublesome to cattle ranchers in some geographical regions. Control of conjunctivitis is important to prevent long term damage to the animals and the value of the herd. Treatment of individual animals when each contracts the infection is expensive and very time consuming. Standard treatment often includes systemic injection of a wide variety of antibiotics, for example 3 milligrams of tetracycline per pound of body weight, and topical application to the eyes. Duration of therapy varies, but treatment normally extends for at least 2 to 3 days.

To reduce cost to the owner and damage to the animals susceptible to conjunctivitis, it is very desirable to provide a method of preventing or at least substantially reducing the likelihood of conjunctivitis in such animals, especially during the peak period for infection, and further to do so in a manner that allows a large group of animals to be treated simultaneously before start of the peak period, at a reasonable cost.

SUMMARY OF THE INVENTION

A method is provided for reducing the risk of conjunctivitis in cattle and other livestock susceptible to such infection. In accordance with the method an antibiotic implant is subcutaneously implanted in close proximity to the eye.

Preferably the implant is implanted above the eye within the eyelid, approximately one half inch from the margin of the eyelid, between the outer skin and the palpebral conjunctival In addition the implant preferably includes a carrier or matrix, such as polymethylmethacrylate, for the antibiotic that provides for slow, continuous release of the antibiotic over approximately a three to four month period. This will allow for release of the antibiotic from time of implant in early July to near the end of October. Carriers suitable for use with the invention include any composition that is both non-harmful to the animal being injected and which will help maintain the antibiotic in pellet form for implantation. Examples of such carriers include diphenylpolysiloxane, dimethylsiloxane, polymethylpolysiloxane, trifluoropropylmethylsiloxane, polydimethylsiloxane, other siloxane polymers, polylactic acid polymers, polyvinyl alcohols with ethylvinyl acetate, polyanhydrides and polyorthoesters.

The quantity of antibiotic is determined to provide an effective delivery over the peak period. For example, 200 milligrams of tetracycline may be utilized for each implant per eye. A range of 160 milligrams to 450 milligrams of tetracycline is preferred.

The antibiotic may be any antibiotic that is effective against normal conjunctivitis associated microbes, especially Moraxella Boris, and that is compatible with the animal to be treated. Typically tetracycline derivatives and related compounds, such as oxytetracycline, are highly effective, and tetracycline is a preferred antibiotic for use in conjunction with the method. Other drugs, such as penicillin and the penicillin family of antibiotics such as ampicillin and amoxicillin as well as antibiotics from the "mycin" family of drugs such as clindamycin, erythromycin, kanimycin, gentamycin, rifamycin, spectinomycin, vancomycin and neomycin, may also be suitable for use in the method according to the invention. Further examples of usable antibiotics include minocycline, chlortetracycline, cephalexin, ceftifur sodium, sulfonomides, bacitracin, tylosin, polymixin B, tilmycosin and florfenicol.

OBJECTS AND ADVANTAGES OF THE INVENTION

Therefore, the objects of the invention of this application are: to provide a method of reducing the likelihood of conjunctivitis in livestock, especially cattle, by placing an antibiotic implant in close proximity to each eye of an animal to be treated in accordance with the method; to provide such a method that reduces the likelihood of conjunctivitis during an extended period, especially a period in the northern hemisphere extending from July to October of each year; to provide such a method wherein the implant includes an antibiotic in a time release matrix; to provide such a method wherein the implant is preferably placed near a lacrimal gland or the Meibomian glands such that the antibiotic will be carried by fluid from the gland across the eye to function as an ophthalmic antibiotic; to provide such a method wherein the implant is placed above an animal's eye, approximately one half inch from the margin of the animal's eyelid; to provide such a method that can be applied to a large group of animals during a short period of time, especially when other procedures are performed on the animals in a control chute, such as tagging, dehorning, etc., and to provide such a method that is comparatively easy to use when compared to treatment of animals subsequent to infection and when applied to a group, comparatively inexpensive to use and especially well adapted for the intended purpose thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

Figure 1:
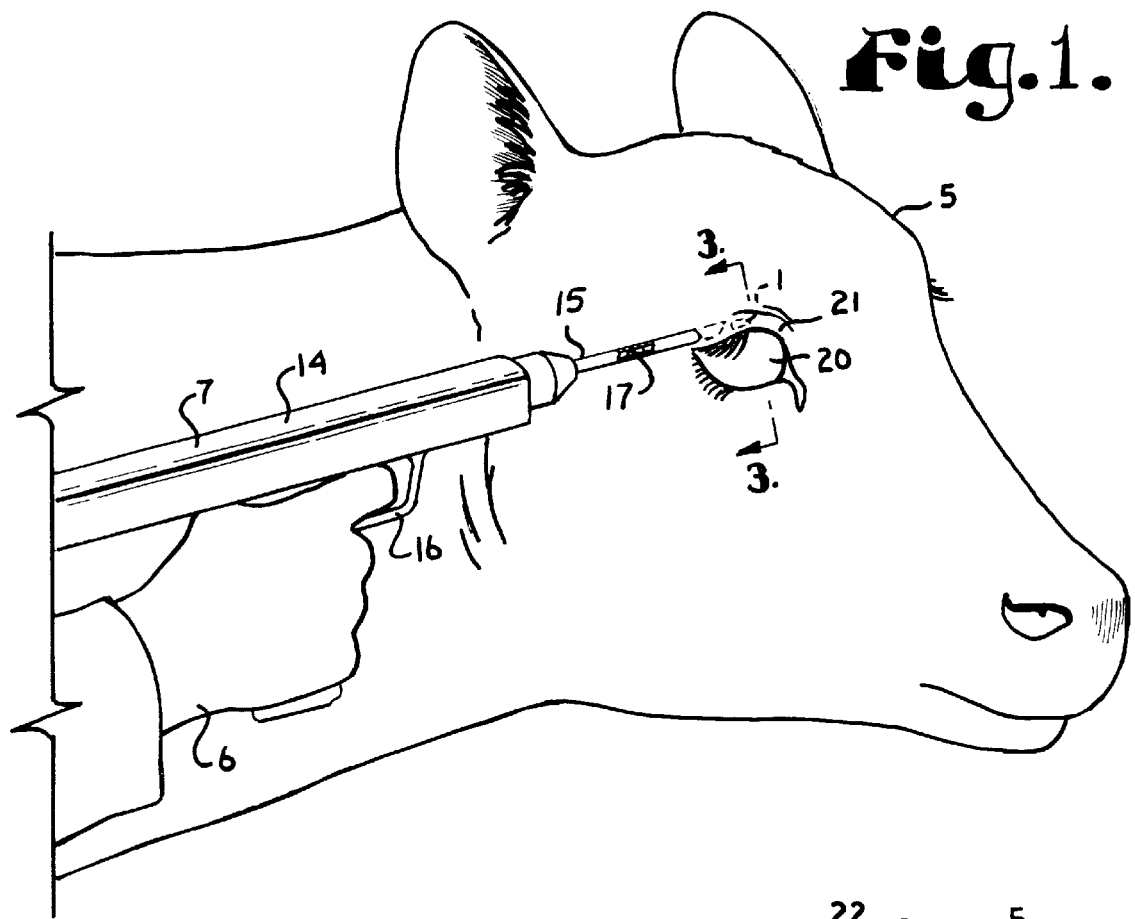
FIG. 1 is a fragmentary perspective view of a cow receiving an antibiotic implant from an implanter in accordance with the method of the present application.
Figure 2:
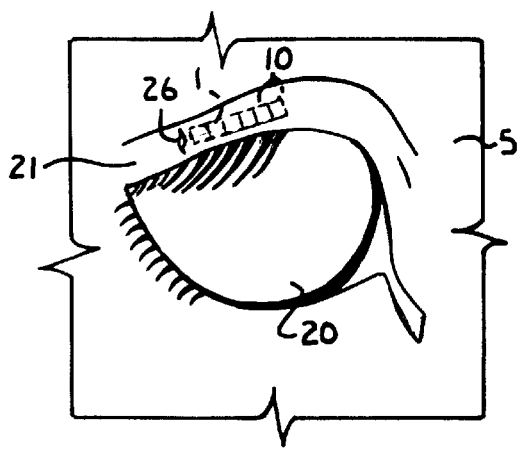
FIG. 2 is an enlarged, fragmentary front elevational view of the cow, showing the implant in phantom lines and the implant's position relative to an eye of the cow.
Figure 3:
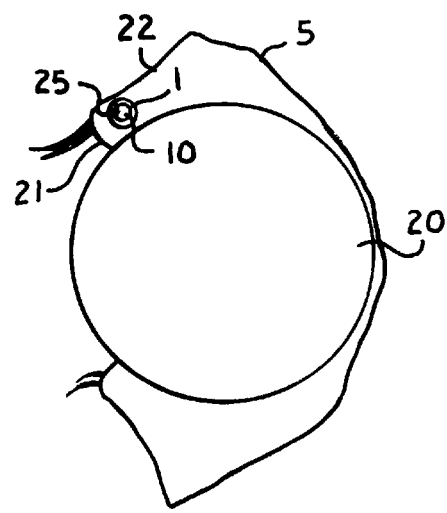
FIG. 3 is a fragmentary cross sectional view of the cow showing the position of the implant, taken along the line 3—3 of FIG. 2.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally represents an implant, utilized in accordance with the method of the present application, implanted in a cow 5 by an operator 6 using an implanter 7.

The implant 1 includes a plurality of cylindrically shaped pellets 10 that are placed end to end to form an over all cylindrically shaped implant 1. The implant includes one or more antibiotics. A wide variety of antibiotics is usable in the invention provided that the antibiotic is effective against the microbe causing the conjunctivitis and compatible with the animal, here the cow 5, being implanted. The tetracycline family of antibiotics is normally highly effective and the present embodiment utilizes tetracycline, although it is foreseen that any of a wide variety of antibiotics, especially those having an antibiotic effect against the various strains of Moraxella Boris may be used.

Each of the illustrated pellets 10 includes the antibiotic tetracycline with a total dosage for each implant being 200 milligrams of tetracycline. It is foreseen that the preferred dosage may vary depending on many factors including length of peak period in a region, antibiotic used, etc. A preferred range of dosage of tetracycline is in the range of from 160 to 450 milligrams per implant 1.

The antibiotic is preferably included in a time release matrix that allows release of the antibiotic from the pellets 10 over a period of time, such as 90 to 120 days. The matrix may include any suitable material for slow release of the antibiotic that is pharmaceutically suitable for use with the animal, here the cow 5, being treated.

The matrix material also normally functions to pelletize the antibiotic. Normally, the antibiotics are crumbly in a generally pure form. Consequently, the matrix allows the antibiotic to retain a pellet shape during and after implantation. A suitable material which was used in the embodiment is polymethylmethacrylate. Many suitable mixtures of antibiotics to matrix are possible. In the present embodiment the pellets 10 are 90% by weight tetracycline and 10% by weight polymethylmethacrylate. Such a mixture was made and placed in a standard pelletizer to form the pellets 10.

The implanter 7 is a conventional implanter for implanting pharmaceutical and related compositions into animals. Such an implanter is shown in U.S. Pat. No. 5,522,797 entitled Slide Action Veterinary Implanter, which is incorporated herein by reference.

The implanter 7 includes a body 14 supporting a needle 15 and having an operating trigger 16. The body 14 operably holds a plurality of pellet implants 1 that are individually delivered through a bore 17 of the needle 15, when the operator 6 squeezes the trigger 16. Preferably the needle 15 is easily removed from the implanter 7 through a threaded connection and the needle 15 is replaced with a sterile new needle for each implantation.

While the exact method of transfer of the antibiotic from the pellets 10 to the eye 20 is not fully understood and it is the intent of applicant to not be limited to a particular method of operation, transfer is believed to occur because the antibiotic in the implant 1 is released over time and thereby produces comparatively high concentrations of the antibiotic in the surrounding tissue with subsequent migration to the surface of the eye. Preferably, the antibiotic becomes absorbed in the fluid that becomes the lacrimal secretions via the vascular system such that a sufficient concentration of antibiotic enters the tear film 20 to produce a minimum antibiotic prophylactic level with respect to microbes associated with pinkeye and, in particular, against Moraxella Bovis.

The illustrated cow 5 has an eye 20 with an eyelid 21. The implant 1 is operably placed by penetrating the skin 22 of the eyelid 21 in close proximity, but spaced from the eye 20 so as not to injure the eye 20. In particular, the implant 1 is inserted into an implant receiving bore 25 made by the needle 15 in the cow 5. The needle 15 penetrates the skin 22 at puncture 26 which leads to the implant receiving bore 25.

In the present embodiment, the implant 1 is placed in the bore 25 approximately one half inch from the margin of the eyelid 21. The implant 1 may be alternatively placed near a lacrimal gland or the Meibomian glands such that fluid from the respective glands enhance transport of the antibiotic in the implant 1 from the bore 25 to the eye 20.

The carrier or matrix within which the antibiotic is placed in the pellets 10 is preferably both inert and biodegradable.

In use the method reduces the likelihood of conjunctivitis. In particular, an implant 1 containing a suitable antibiotic is implanted above each eye 20, preferably in early July or at the beginning of the peak period for conjunctivitis. The antibiotic passes through the surrounding tissue to the eye 20 to operably function as an antibiotic against conjunctivitis-causing microbes. Alternatively the antibiotic is carried by tear or lipid fluids from the lacrimal or Meibomian glands to the eye. Preferably, the antibiotic is released over most of the peak period for conjunctivitis to reduce the presence of conjunctivitis-causing microbes in the eye 20 and thereby reduce the likelihood of incidence of conjunctivitis.

The implant 1 is placed while the cow 5 is restrained by a chute (not shown) or suitable head restraint such as a neck and nose bar or suitable halter.

The following example is provided to illustrate the invention and is not intended to limit the scope of the claims.

EXAMPLE

In accordance with the invention, two cows were selected for testing. Antibiotic pellets were formed including 90% by weight tetracycline and 10% by weight polymethylmethacrylate. An implant was made with a plurality of pellets having a total of approximately 200 milligrams of tetracycline. The implant was subcutaneously placed in the upper eyelids of each of all cows except for one eye in one cow. The implants were placed approximately one half inch from the eyelid margin using an implanter.

A solution was made including live Moraxella Boris bacteria with saline. The solution was first wiped across the four eyes. After a suitable incubation period the eyes were checked and no conjunctivitis was found. The cows were then sedated and the eyes were abraded and retreated with the bacteria solution. Again after an incubation period, the eyes were checked and no conjunctivitis was found.

Finally, the cows were again sedated and the bacterial solution was injected by means of a syringe into the eyeball. Again after a period of time, the eyes were checked for conjunctivitis and none was found, although a small abscess at the site of injection in one eyeball was found.

None of the eyes had conjunctivitis from the time of the above noted testing in early July through the end of October.

It is to be understood that while certain forms of the present invention have been illustrated and described herein, it is not to be limited to the specific forms or arrangement of parts described and shown.

What is claimed and desired to be secured by Letters Patent is as follows:

1. A method of reducing the risk of conjunctivitis in an animal comprising the steps of:
    a) preparing an implant containing an antibiotic having activity against microbes causing conjunctivitis; and
    b) placing the implant subcutaneously in the animal in close proximity to an eye of the animal.
2. The method according to claim 1 including the step of:
    a) implanting of said implants under the skin above each eye of the animal.
3. The method according to claim 1 including the step of:
    a) implanting the implant near a lacrimal gland of the animal.
4. The method according to claim 1 including the step of:
    a) implanting the implant near the Meibomian glands in the eyelid of the animal.
5. The method according to claim 1 wherein:
    a) the implant is time released and implanted near the eye at about the beginning of the peak infection period for pinkeye in a geographic region.
6. The method according to claim 1 wherein:
    a) the implant includes a matrix adapted to allow continuous release over time of the antibiotic over at least one month.
7. The method according to claim 6 wherein:
    a) the matrix releases the antibiotic over approximately four months.
8. The method according to claim 7 wherein:
    a) the antibiotic is chosen from the tetracycline family of antibiotics and pharmaceutically active derivatives thereof.
9. The method according to claim 1 including:
    a) selecting tetracycline as the antibiotic.
10. The method according to claim 9 including:
    a) initially pelletizing the antibiotic with a polymethylmethacrylate matrix prior to injecting into the animal.
11. The method according to claim 1 wherein:
    a) the animal is a cow.
12. The method according to claim 11 including:
    a) injecting a plurality of animals with the implant over a short period of time and in conjunction with other activities involving the animals.

* * * * *